# (12) United States Patent
Kawakami

(10) Patent No.: US 8,979,816 B2
(45) Date of Patent: Mar. 17, 2015

(54) DISPOSABLE WEARING ARTICLE COMPRISING A VARIABLE STIFFNESS REGION

(75) Inventor: Yusuke Kawakami, Kanagawa (JP)

(73) Assignee: Unicharm Corporation, Ehime (JP)

( * ) Notice: Subject to any disclaimer, the term of this patent is extended or adjusted under 35 U.S.C. 154(b) by 272 days.

(21) Appl. No.: 13/643,636

(22) PCT Filed: May 17, 2011

(86) PCT No.: PCT/JP2011/061338
§ 371 (c)(1),
(2), (4) Date: Oct. 26, 2012

(87) PCT Pub. No.: WO2011/145626
PCT Pub. Date: Nov. 24, 2011

(65) Prior Publication Data
US 2013/0046266 A1   Feb. 21, 2013

(30) Foreign Application Priority Data
May 20, 2010   (JP) ................................ 2010-116693

(51) Int. Cl.
*A61F 13/49* (2006.01)
*A61F 13/496* (2006.01)
*A61F 13/539* (2006.01)

(52) U.S. Cl.
CPC ......... *A61F 13/496* (2013.01); *A61F 13/49011* (2013.01); *A61F 13/4906* (2013.01); *A61F 13/539* (2013.01); *A61F 2013/49066* (2013.01)
USPC .............. 604/385.3; 604/385.24; 604/385.29; 604/394

(58) Field of Classification Search
CPC .................... A61F 13/49011; A61F 13/49019; A61F 13/72; A61F 2013/49025
USPC ............. 604/385.24, 385.29, 385.3, 394, 396
See application file for complete search history.

(56) References Cited

U.S. PATENT DOCUMENTS 5,545,158 A * 8/1996 Jessup ......................... 604/385.3
6,083,212 A * 7/2000 Kumasaka ................ 604/385.29
(Continued)

FOREIGN PATENT DOCUMENTS

| CA | 2812969 A1 | 12/2007 |
| EP | 1188427 A1 | 3/2002 |

(Continued)

OTHER PUBLICATIONS

Supplementary European Search Report issued Apr. 1, 2014, corresponds to European patent application No. 11783560.3.
(Continued)

*Primary Examiner* — Tan-Uyen (Jackie) T Ho
*Assistant Examiner* — Kathryn E Ditmer
(74) *Attorney, Agent, or Firm* — Lowe Hauptman & Ham LLP

(57) ABSTRACT

A disposable wearing article includes front and rear outer sheets, an inner sheet, and front and rear waist-opening sheets. Each of first sheet segments of the waist-opening sheets is longer than the corresponding second sheet segments. End portions are bonded to outer surfaces of the outer sheets. In areas where the end portions are spaced apart from the front and rear outer sheets, the first sheet segments and the inner sheet are overlapped to form low stiffness sub-regions. In respective sides inboard of the low stiffness sub-regions, the inner sheet, the front and rear outer sheets and the first sheet segments are respectively overlapped to form inner high stiffness sub-regions, and in respective sides outboard of the low stiffness sub-regions, the inner sheet, the second sheet segments and the first sheet segments are overlapped to form outer high stiffness sub-regions.

5 Claims, 5 Drawing Sheets

(56) References Cited

U.S. PATENT DOCUMENTS

| | | | |
|---|---|---|---|
| 6,306,122 B1* | 10/2001 | Narawa et al. | 604/385.3 |
| 6,336,921 B1* | 1/2002 | Kato et al. | 604/385.3 |
| 8,187,244 B2* | 5/2012 | Saito | 604/385.31 |
| 2003/0176846 A1* | 9/2003 | Karami | 604/385.29 |
| 2005/0014428 A1 | 1/2005 | Zenker et al. | |
| 2007/0255246 A1 | 11/2007 | Schneider | |
| 2007/0265591 A1* | 11/2007 | Loritz et al. | 604/361 |
| 2007/0282292 A1* | 12/2007 | Harkness | 604/396 |
| 2008/0134487 A1* | 6/2008 | Hartono | 29/428 |

FOREIGN PATENT DOCUMENTS

| | | |
|---|---|---|
| JP | 2005237782 A | 9/2005 |
| JP | 2005287693 A | 10/2005 |
| JP | 2008245884 A | 10/2008 |
| JP | 2008295838 A | 12/2008 |

OTHER PUBLICATIONS

International Search Report and Written Opinion corresponding to PCT/JP2011/061338, dated Aug. 2, 2011.

* cited by examiner (a)

(b)

DISPOSABLE WEARING ARTICLE COMPRISING A VARIABLE STIFFNESS REGION

RELATED APPLICATIONS

The present application is a National Phase of International Application Number PCT/JP2011/061338, filed May 17, 2011, and claims priority from, Japanese Application Number 2010-116693, filed May 20, 2010.

TECHNICAL FIELD

The present invention relates to disposable wearing articles and, more specifically, to disposable wearing articles, for example, disposable diapers, toilet-training pants and incontinence briefs each provided with a plurality of elastics in waist regions.

BACKGROUND

Conventionally, disposable wearing articles in the form of disposable diapers having front and rear waist regions respectively provided with a plurality of elastics are known. For example, JP 2008-245884 A (PTL 1) discloses a disposable diaper including a plurality of elastics attached to the front and rear waist regions so as to extend in a transverse direction and to be spaced apart from each other in a longitudinal direction. The diaper is formed in the front and rear waist regions, respectively, with slip compensating buffer zones each composed of a set of elastics arranged at pitches in the longitudinal direction larger than those at which the adjacent set of elastics.

CITATION LIST

Patent Literature

{PTL 1}: JP 2008-245884 A

SUMMARY

In the diaper disclosed in PTL 1, the front and rear waist regions are respectively formed of an upper layer nonwoven fabric and a lower layer nonwoven fabric between which the elastics are attached. In each of the slip compensating buffer zones, ridges and grooves both extending in the longitudinal direction are developed to form gathers by contraction of the elastics. These gathers enhance the stiffness in the slip compensating buffer zones, making it difficult to develop wrinkles which would function particularly to shorten the dimension in the longitudinal direction, in other words, which would extend in the transverse direction.

An object of the present invention is to provide a disposable wearing article adapted to be easily folded along fold lines extending in a transverse direction formed at at least one of front and rear waist regions.

Some embodiments of the present invention provide a disposable wearing article having a longitudinal direction and a transverse direction, the article including:
 a skin-facing side;
 a non-skin-facing side opposite to the skin-facing side;
 a chassis including a front waist region, a rear waist region and a crotch region extending between the front and rear waist regions;
 an absorbent structure lying at least in the crotch region;
 a waist-opening defined by front and rear ends of the chassis; and
 leg-openings defined by lateral edges of the chassis, wherein a plurality of front and rear waist elastics extending in the transverse direction and spaced apart from each other in the longitudinal direction are contractibly attached under tension to the front and rear waist regions.

This invention further includes the following features:
 the chassis includes a plurality of sheets layered one another;
 at least one of the front and rear waist regions is formed with a variable stiffness region including a low stiffness sub-region extending in the transverse direction and a pair of high stiffness sub-regions being adjacent to both sides of the low stiffness sub-regions as viewed in the longitudinal direction, wherein the variable stiffness region is segmented by a pair of the waist elastics; and
 the number of the sheets overlapped to form the low stiffness sub-region is fewer than the number of the sheets to form the respective high stiffness sub-regions.

According to an embodiment of this invention, distances at which a pair of the waist elastics laying out the respective variable stiffness regions are arranged are larger than those at which other waist elastics lying outboard of the respective variable stiffness regions as viewed in the longitudinal direction are arranged.

According to another embodiment of this invention, the waist elastics laying out the respective variable stiffness regions lie so as to overlap ends of the layered sheets.

According to even another embodiment of this invention, the chassis includes:
 an inner sheet lying on the skin-facing side;
 an outer sheet lying on the non-skin-facing side; and
 a waist-opening sheet adapted to define the waist-opening in at least one of the front and rear waist regions, wherein:
 the waist opening sheet includes:
 a first sheet segment lying on the non-skin-facing side; a second sheet segment lying on the skin-facing side; and
 a boundary lying between the first and second sheet segments so as to coincide with the waist-opening, wherein:
 the first sheet segment overlaps both the inner sheet and the outer sheet;
 the second sheet segment overlaps the inner sheet, and the second sheet segment and the outer sheet are arranged so as to be spaced apart from each other in the longitudinal direction;
 the low stiffness sub-region is defined by a region in which the second sheet segment and the outer sheet are spaced apart from each other;
 the respective high stiffness regions are defined by a region in which the first sheet segment, the second sheet segment and the inner sheet are overlapped, and also by a region in which the second sheet segment, the outer sheet and the inner sheet are overlapped.

According to still another embodiment of this invention, a dimension in the longitudinal direction of the respective low stiffness sub-region is in a range of 1 mm to 10 mm.

According to yet another embodiment of this invention, a dimension in the longitudinal direction of the respective variable stiffness regions is in a range of 20 mm to 35 mm.

ADVANTAGEOUS EFFECTS OF INVENTION

According to this invention, particularly according to one or more embodiments thereof, at least one of the front and rear waist regions is formed with the variable stiffness region including the low stiffness sub-region extending in the transverse direction and a pair of high stiffness sub-regions lying adjacent to the both sides of the low stiffness sub-region as viewed in the longitudinal direction wherein the variable stiffness region is segmented by a pair of the waist elastics spaced apart from each other in the longitudinal direction. With such an arrangement, the wearing article is easily folded along the low stiffness sub-region.

DESCRIPTION OF EMBODIMENTS

Figure 1:
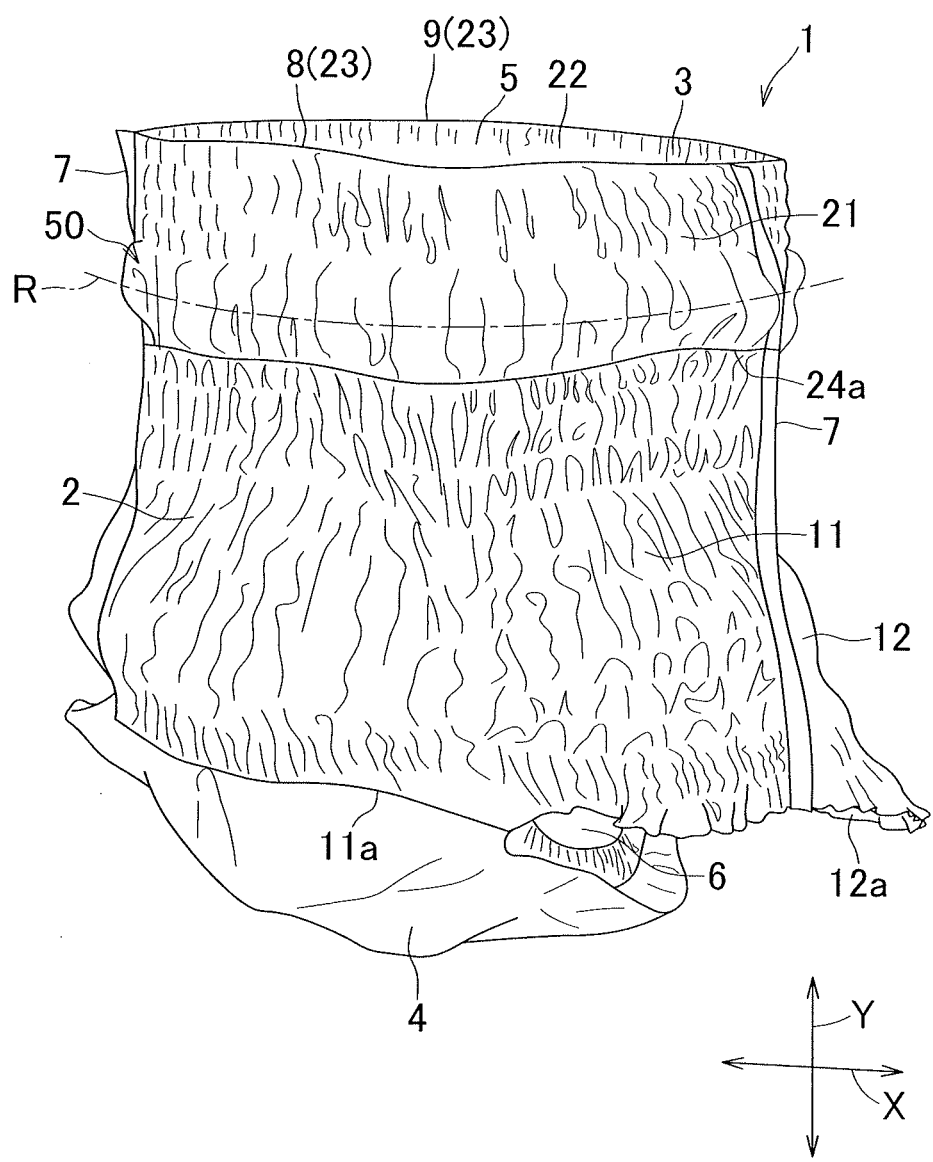
FIG. 1 is a perspective view of a disposable diaper as an example of the disposable wearing article.
Figure 2:
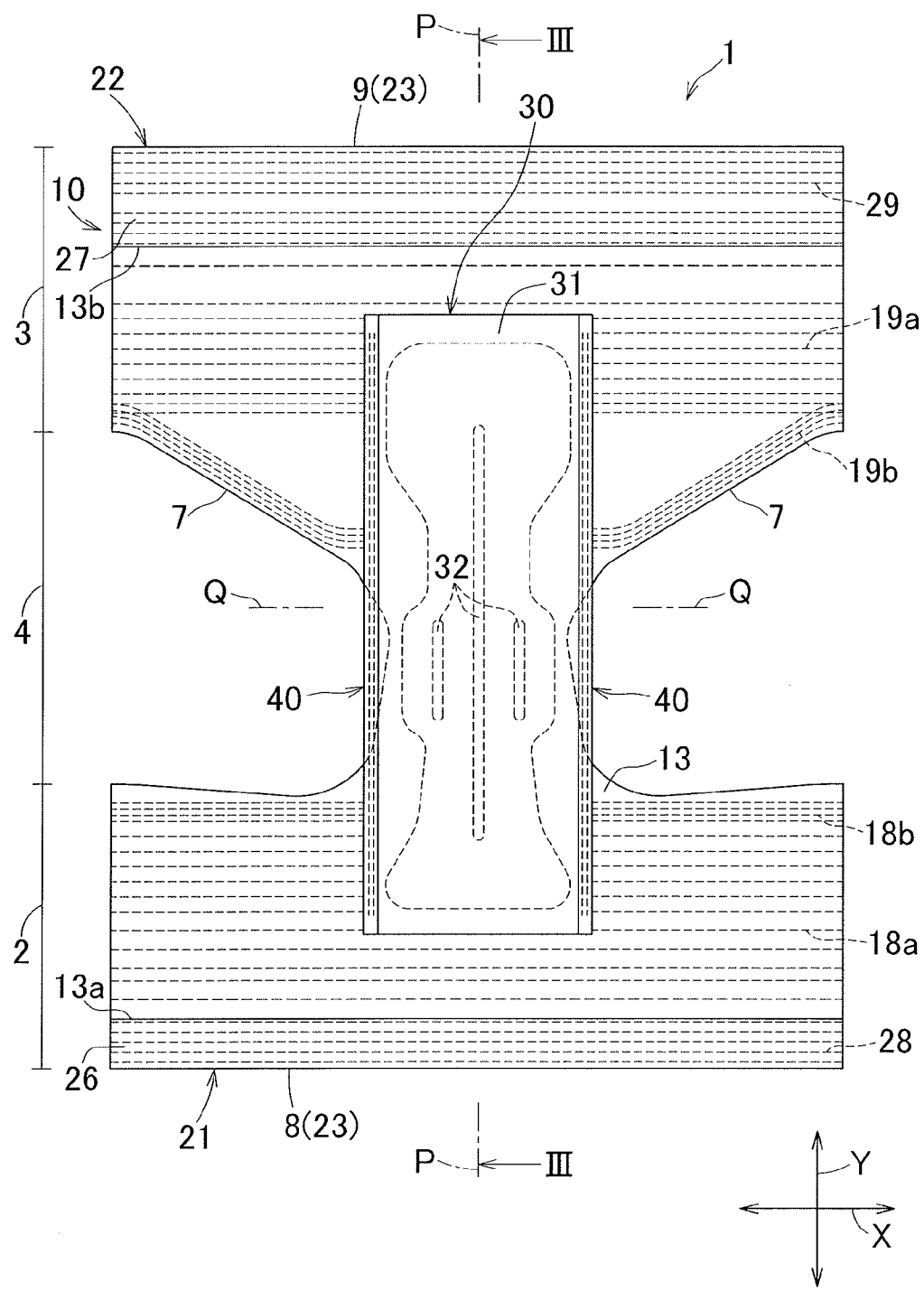
FIG. 2 is a developed plan view of the diaper.
Figure 3:
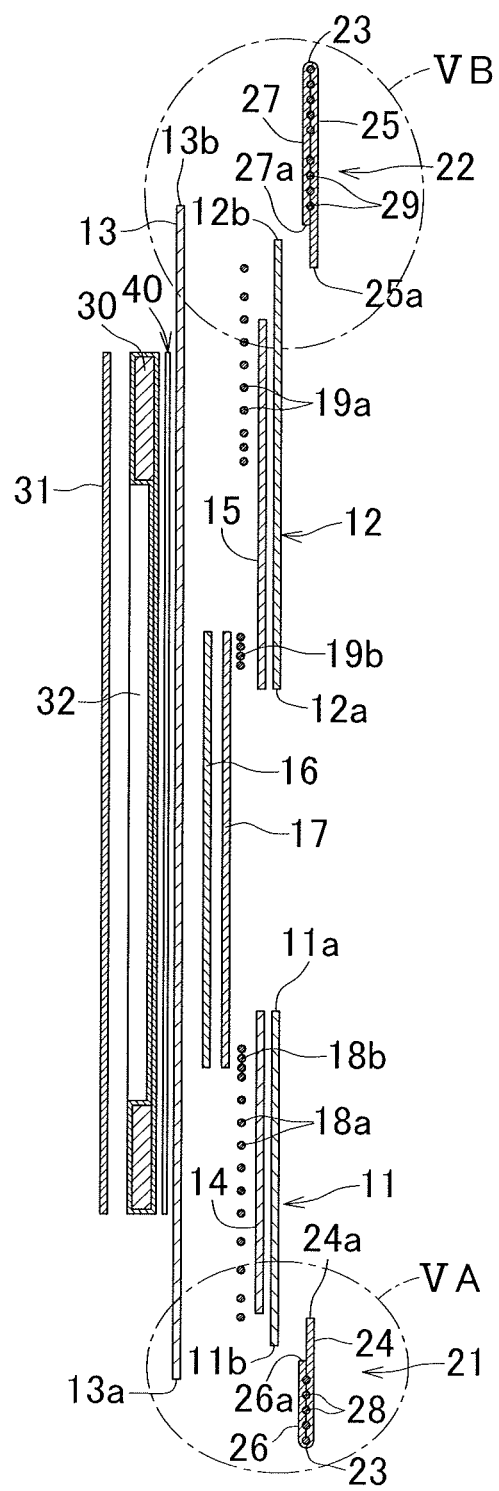
FIG. 3 is a schematic sectional view taken along line in FIG. 2.
Figure 4:
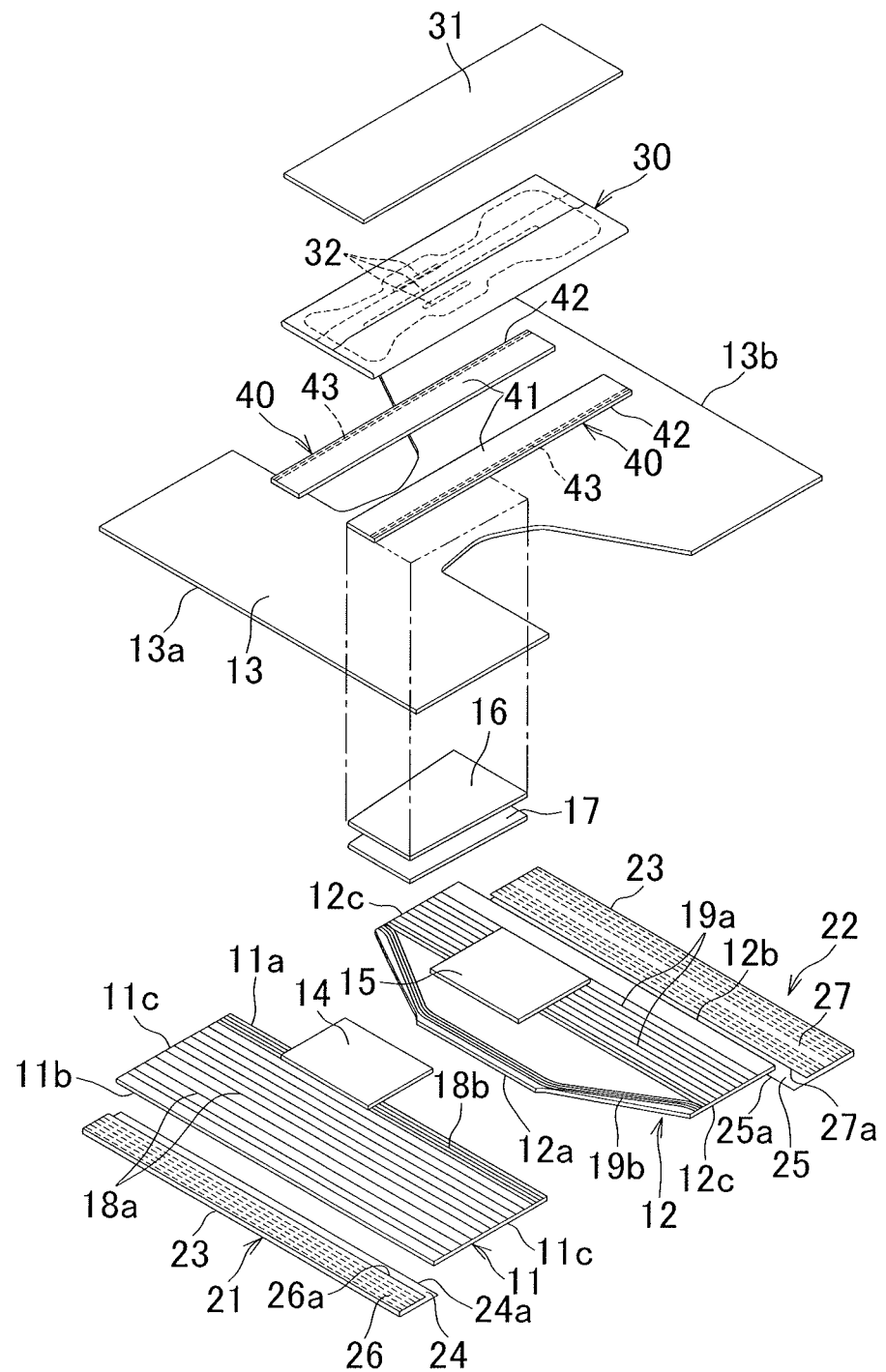
FIG. 4 is an exploded perspective view corresponding to FIG. 2.
Figure 5:
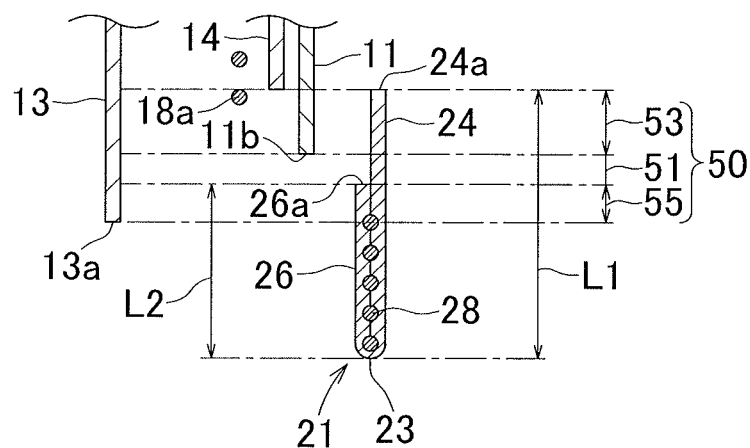
FIG. 5(a) is a scale-enlarged diagram illustrating an encircled portion VA in FIG. 3.
FIG. 5(b) is a scale-enlarged diagram illustrating an encircled portion VB in FIG. 3.
Figure 5:
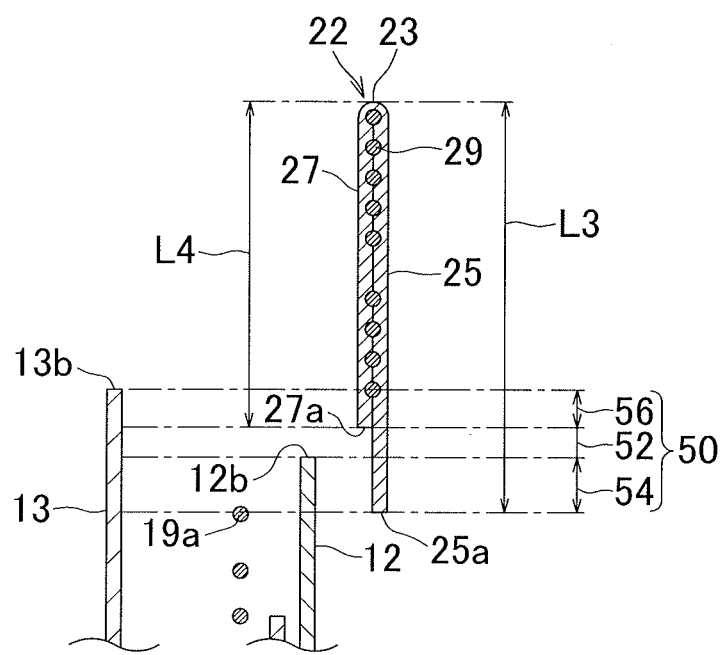

FIGS. 1 through 5 illustrate an embodiment of this invention and, with reference to FIGS. 1 through 5, a disposable diaper will be described hereunder as an example of the disposable wearing articles according to this invention. FIG. 1 is a perspective view illustrating the diaper 1 with a waist-opening 5 as well as leg-openings 6 being kept in annular states, respectively. FIG. 2 is a developed plan view of the diaper 1 as viewed from the skin-facing side wherein the diaper 1 is kept flat with respective elastics of the diaper being stretched against contractile force thereof. FIG. 3 is a sectional view taken along line in FIG. 2, schematically illustrating the diaper with respective constituent sheets being spaced apart from each other. FIG. 4 is an exploded perspective view corresponding to FIG. 2. FIG. 5(a) is a scale-enlarged diagram illustrating an encircled portion VA in FIG. 3 and FIG. 5(b) is a scale-enlarged diagram illustrating an encircled portion VB in FIG. 3.

The diaper 1 has a longitudinal direction Y and a transverse direction X and includes a skin-facing side, a non-skin-facing side opposite to the skin-facing side. i.e., a garment-facing side, a front waist region 2, a rear waist region 3, a crotch region 4 extending between the front and rear waist regions 2, 3. The front and rear waist regions 2, 3 are bonded to each other along respective pairs of lateral edges 7 thereof and thereupon front and rear ends 8, 9 of the diaper 1 extending in the transverse direction X cooperate with each other to form the waist-opening 5 and segments of the lateral edges 7 extending in the crotch region 4 cooperate with each other to form the leg-openings 6. The diaper 1 has, in addition, a longitudinally extending imaginary center line P-P bisecting a dimension in the longitudinal direction Y of the diaper 1 and a transversely extending imaginary center line Q-Q bisecting a dimension of the diaper 1 in the longitudinal direction Y wherein the diaper 1 is formed so as to be substantially symmetric about the longitudinally extending imaginary center line P-P. The lateral edges 7 are curved toward the longitudinally extending imaginary center line P-P in the crotch region 4 so that a dimension of the crotch region 4 in the transverse direction may be gradually reduced.

The diaper 1 further includes a chassis 10 having the front and rear waist regions 2, 3 and the crotch region 4, an absorbent structure 30 lying on the skin-facing side of the chassis 10 and extending across the crotch region 4 into the front and rear waist regions 2, 3, and leakage-barrier cuffs 40.

The chassis 10 includes front and rear outer sheets 11, 12 lying on the garment-facing side and partially defining the front and rear waist regions 2, 3, an inner sheet 13 lying on the inner of the front and rear outer sheets 11, 12 and partially overlapping these outer sheets 11, 12 so as to define the crotch region 4 and respective parts of the front and rear waist regions 2, 3. The front and rear outer sheets 11, 12 are spaced apart from each other in the longitudinal direction Y and the inner sheet 13 is located so as to connect these two sheets 11, 12 to each other. As material of the front and rear outer sheets 11, 12 and the inner sheet 13, for example, a hydrophobic spunbonded fibrous nonwoven fabric or an SMS (spunbonded-meltblown-spunbonded) fibrous nonwoven fabric may be used.

The front outer sheet 11 has inner and outer ends 11a, 11b extending in the transverse direction X and lateral edges 11c extending in the longitudinal direction Y to define a substantially rectangular shape as a whole. The rear outer sheet 12 has inner and outer ends 12a, 12b extending in the transverse direction X and lateral edges 12c extending in the longitudinal direction Y wherein the front and rear outer sheets 11, 12 are in such a dimensional relationship that, when the respective outer ends 11b, 12b of the front and rear outer sheets 11, 12 are overlapped with each other, the inner end 12a of the rear outer sheet 12 extends outward beyond the inner end 11a of the front outer sheet 11. This protruding region has a substantially trapezoidal shape.

Between the front and rear outer sheets 11, 12 and the inner sheet 13, there are provided a front leakage-barrier sheet 14 bonded to the front outer sheet 11, a rear leakage-barrier sheet 15 bonded to the rear outer sheet 12 and a crotch leakage-barrier sheet 16 located between these front and rear leakage-barrier sheets 14, 15 as viewed in the longitudinal direction Y wherein a cover sheet 17 is bonded to the side of the crotch leakage-barrier sheet 16. As material of these leakage-barrier sheets 14, 15, 16, for example, a hydrophobic and breathable plastic film may be used and thereby leakage of bodily fluids such as urine out of the diaper 1 may be prevented. The crotch leakage-barrier sheet 16 and the cover sheet 17 are substantially the same in shape as well as size wherein, as material of the cover sheet 17, for example, a hydrophobic fibrous nonwoven fabric may be used. The respective outer surfaces of the front and rear leakage-barrier sheets 14, 15 may be covered with the front and rear outer sheets 11, 12, respectively, and the outer surface of the crotch leakage-barrier sheet 16 may be covered with the cover sheet 17 to improve the texture of the diaper 1 on the garment-facing side. As means for bonding the respective sheets to each other, for example, hot melt adhesives may be used.

A plurality of front waist elastics 18a and front leg elastics 18b are contractibly attached under tension in the transverse direction X between the front outer sheet 11 and the inner sheet 13. The front leg elastics 18b are attached along the inner end 11a and the front waist elastics 18a are attached so as to be adjacent to the front leg elastics 18b in the longitudinal direction Y and on the side of the outer end 11b. Both the front waist elastics 18a and the front leg elastics 18b are arranged so as to be spaced apart from each other in the longitudinal direction Y and are bonded to at least one of the front outer sheet 11 and the inner sheet 13 by suitable bonding means such as hot melt adhesives.

A plurality of rear waist elastics 19a and rear leg elastics 19b are contractibly attached under tension between the rear outer sheet 12 and the inner sheet 13. The rear waist elastics 19a are contractibly attached under tension in the transverse direction X and arranged to be spaced apart from each other in the longitudinal direction Y. The rear leg elastics 19b are contractibly attached under tension along the inner end 12a of the rear outer sheet 12 and arranged to be spaced apart from each other. Both the rear waist elastics 19a and the rear leg elastics 19b are bonded to at least one of the rear outer sheet 12 and the inner sheet 13 by suitable bonding means such as hot melt adhesives.

Front and rear waist-opening sheets 21, 22 are bonded to respective outer surfaces of the front and rear outer sheets 11, 12 as viewed in the longitudinal direction Y. More specifically, the front waist-opening sheet 21 is bonded to the outer surface of the outer end 11b of the front outer sheet 11 and the rear waist-opening sheet 22 is bonded to the outer surface of the outer end 12b of the rear outer sheet 12. The front and rear waist-opening sheets 21, 22 are respectively divided along respective boundaries 23 into first sheet segments 24, 25 lying on the outer surface side and second sheet segments 26, 27 lying on the inner surface side. More specifically, the front and rear waist-opening sheets 21, 22 are folded along the respective boundaries 23 and the first sheet segments 24, 25 and the second sheet segments 26, 27 are layered to each other, respectively. The boundaries 23 define the waist-opening 5 and, at the same time, define the front and rear ends 8, 9 of the chassis 10 (See FIG. 1).

An absorbent structure 30 is attached to the inner surface side of the inner sheet 13. The absorbent structure 30 includes a core composed of at least one of fluff pulp, superabsorbent polymer particles and a mixture thereof, and tissue paper or the like wrapping the core, wherein a body side liner 31 lies on an absorption side of the absorbent structure 30 to cover the core. As material of the body side liner 31, a liquid-pervious fibrous nonwoven fabric, for example, an air-through nonwoven fabric or a spunbonded nonwoven fabric may be used. The absorbent structure 30 is formed with a plurality of grooves 32 extending in the longitudinal direction Y. In a region of the absorbent structure 30 formed with the grooves 32, substantially no or scarce core material is present, and thereby the absorbent structure 30 may be easily folded along these grooves 32 and easily put in close contact with the wearer's body. Further, formation of the grooves 32 makes it possible to enlarge the absorption area of the core and thereby to accelerate absorption of bodily fluids such as urine.

A pair of leakage-barrier cuffs 40 is interposed between the absorbent structure 30 and the inner sheet 13. The leakage-barrier cuffs 40 are arranged to be spaced apart from each other in the transverse direction X and to extend in the longitudinal direction Y. In each of the leakage-barrier cuffs 40, an inner lateral edge 41 lying inner side as viewed in the transverse direction X is bonded between the absorbent structure 30 and the inner sheet 13, and an outer lateral edge 42 lying outer side as viewed in the transverse direction X is provided with a plurality of cuff elastics 43 extending in the longitudinal direction Y and contractibly attached thereto under tension in the longitudinal direction Y. The outer lateral edge 42 is not bonded to the inner sheet 13 and adapted to be spaced upward from the inner sheet 13 under contraction of the cuff elastics 43 so as to come in close contact with vicinities of the wearer's inguinal regions and thereby to prevent bodily fluids such as urine from leaking out of the diaper.

FIG. 5(a) and FIG. 5(b) are scale-enlarged diagrams respectively illustrating the encircled portions VA and VB in FIG. 3. The front and rear waist-opening sheets 21, 22 are respectively formed so that dimensions in the longitudinal direction Y of the first sheet segments 24, 25 may be larger than those of the second sheet segments 26, 27. Specifically, in the front waist-opening sheet 21, a length dimension L1 of the first sheet segment 24 measured from an end 24a to the boundary 23 maybe in a range of about 60 to about 85 mm and, in the illustrated embodiment, this length dimension L1 is set to about 64.5 mm. A length dimension L2 of the second sheet segment 26 measured from an end 26a to the boundary 23 may be in a range of about 40 to about 70 mm and, in the illustrated embodiment, this length dimension L2 is set to about 42 mm. A dimensional difference between these first and second sheet segments 24, 26 may be in a range of about 15 to about 30 mm and, in the illustrated embodiment, this dimensional difference is set to about 22.5 mm. In the rear waist-opening sheet 22, a length dimension L3 of the first sheet segment 25 measured from an end 25a to the boundary 23 may be in a range of about 100 to about 125 mm and, in the illustrated embodiment, this length dimension L3 is set to about 104.5 mm. A length dimension L4 of the second sheet segment 27 measured from an end 27a to the boundary 23 may be in a range of about 80 to about 100 mm and, in the illustrated embodiment, this dimension L4 is set to about 82 mm. A dimensional difference between these first and second sheet segments 25, 27 may be in a range of about 15 to about 30 mm and, in the illustrated embodiment, this dimensional difference is set to about 22.5 mm.

Between each pair of the first sheet segments 24, 25 and the second sheet segments 26, 27, a plurality of front and rear waist-opening elastics 28, 29 are respectively arranged so as to be spaced apart from each other in the longitudinal direction Y. These front and rear waist-opening elastics 28, 29 extend in the transverse direction X and contractibly attached under tension. The front waist-opening elastics 28 are arranged in an area defined between the boundary 23 and a line at a distance of about 32 mm in the longitudinal direction Y and are spaced apart from the ends 24a, 26a of the first and second sheet segments 24, 26, respectively. The rear waist-opening elastics 29 are arranged in an area defined between the boundary 23 and a line at a distance of about 72 mm in the longitudinal direction Y and are spaced apart from the ends 25a, 27a of the first and second sheet segments 25, 27, respectively. According to this embodiment, the front and rear waist-opening elastics 28, 29, the front and rear waist elastics 18a, 19a and the front and rear leg elastics 18b, 19b cooperate together to constitute the waist elastics according to this invention.

The front and rear waist-opening sheets 21, 22 are laminated on the respective outer surfaces of the front and rear outer sheets 11, 12 in such a manner that the respective ends 24a, 25a of the first sheet segments 24, 25 overlap the respective outer surfaces of the front and rear outer sheets 11, 12 and are bonded thereto, but the respective ends 26a, 27a of the second sheet segments 26, 27 are spaced apart from the front and rear outer sheets 11, 12. In other words, the end 26a of the second sheet segment 26 and the outer end 11b of the front outer sheet 11 are spaced apart from each other in the longitudinal direction Y without coming in contact with each other. In a similar fashion, the end 27a of the second sheet segment 27 and the outer end 12b of the rear outer sheet 12 are spaced apart from each other in the longitudinal direction Y without coming in contact with each other. A distance between these ends 26a, 27a and the respective outer ends 11b, 12b may be in a range of about 1 to about 10 mm and, in the illustrated embodiment, this distance is set to about 8 mm.

The inner sheet 13 has a size such that a front end 13a thereof may extend beyond the end 26a so as to overlap the first sheet segment 26, and a rear end 13b may extend beyond the end 27a so as to overlap the first sheet segment 27. Specifically, a dimension in the longitudinal direction Y of the inner sheet 13 may be in a range of about 600 to about 650 mm and, in the illustrated embodiment, this dimension is set to about 620 mm.

In a space defined between the respective ends 26a, 27a of the second sheet segments 26, 27 and the front and rear outer sheets 11, 12, only two sheets, i.e., the first sheet segments 24, 25 and the inner sheet 13 are overlapped to define low stiffness sub-regions 51, 52. A dimension in the longitudinal direction Y of the respective low stiffness sub-regions 51, 52 corresponds to a dimension by which the outer ends 11b, 12b are spaced apart from the ends 26a, 27a, respectively. Specifically, the dimension in the longitudinal direction Y of the respective low stiffness sub-regions 51, 52 may be in a range of about 1 to about 10 mm and, in the illustrated embodiment, this dimension is set to about 8 mm (See paragraph {0028}). In respective sides inner than the low stiffness sub-regions 51, 52 as viewed in the longitudinal direction Y, the inner sheet 13, the front outer sheet 11 or the rear outer sheet 12 and the first sheet segment 24 or 25 are respectively overlapped to define three-layered inner high stiffness sub-regions 53, 54. A dimension in the longitudinal direction Y of the respective inner high stiffness sub-regions 53, 54 may be in a range of about 10 to about 20 mm and, in the illustrated embodiment, this dimension is set to about 15 mm. In respective sides outer than the low stiffness sub-regions 51, 52 as viewed in the longitudinal direction Y, the inner sheet 13, the second sheet segment 26 or 27 and the first sheet segment 24 or 25 are overlapped to define three-layered outer high stiffness sub-regions 55, 56. A dimension in the longitudinal direction Y of the respective outer high stiffness sub-regions 55, 56 may be in a range of about 10 to about 20 mm and, in the illustrated embodiment, this dimension is set to about 10 mm.

In the regions of the aforementioned diaper 1 in which the front and rear waist-opening sheets 21, 22 are attached to the front and rear waist regions 2, 3, respectively, the number of sheets overlapped is fewer in the low stiffness sub-regions 51, 52 than in the inner and outer high stiffness sub-regions 53 through 56 which are adjacent to the low stiffness sub-regions 51, 52, respectively, and the stiffness is correspondingly lower in the sub-regions 51, 52 than in the sub-regions 53 through 56. These low stiffness sub-regions 51, 52 and the inner and outer high stiffness sub-regions 53 through 56 respectively extend across the front and rear waist regions 2, 3 in the transverse direction X and constitute respective variable stiffness regions 50.

The front and rear waist elastics 18a, 19a may lie outboard of at least the low stiffness sub-regions 51, 52 in the longitudinal direction Y and, in the illustrated embodiment, the respective outermost ones in the longitudinal direction Y of the front and rear waist elastics 18a, 19a are placed at the positions substantially corresponding to the ends 24a, 25a of the first sheet segments 24, 25 and the remaining elastics are arranged at the positions inside these ends 24a, 25a in the longitudinal direction Y. A distance in the longitudinal direction Y between these front and rear waist elastics 18a, 19a and the front and rear waist-opening elastics 28, 29 may be in a range of about 20 to about 35 mm and, in the illustrated embodiment, this distance is set to about 33 mm wherein the respective variable stiffness regions 50 are segmented by the front and rear waist elastics 18a, 19a opposite to one another in the longitudinal direction Y and the front and rear waist-opening elastics 28, 29 opposite to one another in the longitudinal direction Y. Specifically, a dimension in the longitudinal direction Y of the respective variable stiffness regions 50 may be in a range of about 20 to about 35 mm and, in the illustrated embodiment, this dimension is set to about 33 mm.

A pitch in the longitudinal direction Y at which the front and rear waist elastics 18a, 19a are respectively arranged is set to in a range of about 5 to about 15 mm and this pitch is smaller than the dimension in the longitudinal direction Y of the respective variable stiffness regions 50. In a similar fashion, a pitch in the longitudinal direction Y at which the front and rear waist-opening elastics 28, 29 are respectively arranged is set to in a range of about 5 to about 10 mm and this pitch is also smaller than the dimension in the longitudinal direction Y of the respective variable stiffness regions 50. In this regard, the term "pitch" used herein (and will be used hereunder also) means a center-to-center distance between each pair of the adjacent elastics.

The variable stiffness regions 50 formed in the front and rear waist regions 2, 3 of the aforementioned diaper 1 ensures that, for example, when the front and rear waist regions 2, 3 of the diaper 1 slip toward the side of the crotch region 4 during use the diaper 1, the front and rear waist regions 2, 3 are apt to be folded along the low stiffness sub-regions 51, 52 so that these low stiffness sub-regions 51, 52 may protrude outward. More specifically, the front and rear waist regions 2, 3 are folded along an imaginary line R along which the low stiffness sub-regions 51, 52 extend (See FIG. 1). Adjacent to the low stiffness sub-regions 51, 52, the high stiffness sub-regions 53 through 56 are defined by the front and rear waist elastics 18a, 19a and the front and rear waist-opening elastics 28, 29, respectively. With such an arrangement, in the high stiffness sub-regions 53 through 56 lying closer to the elastics, folds extending in the longitudinal direction Y are developed under contraction of the respective elastics but any fold extending in the transverse direction X is hardly developed. In this way, it is ensured that the front and rear waist regions 2, 3 are easily folded exclusively along the low stiffness sub-regions 51, 52.

When the front and rear waist regions are folded along the low stiffness sub-regions 51, 52, voids are defined between the folded portions and the wearer's body and thereby the diaper 1 is partially spaced apart from the wearer's body. As a result, a ventilation property of the diaper 1 is improved, thereby preventing a skin eruption and an uncomfortable stuffiness. In addition, when the wearer intends to pull up the diaper 1, the wearer's fingers are caught without effort by the folded low stiffness sub-regions 51, 52 and the wearer can easily pull up the diaper. For the reason that the high stiffness sub-regions 53 through 56 are adjacent to the low stiffness sub-regions 51, 52, respectively, even if the wearer violently pulls up the diaper 1, the diaper 1 should not be torn.

For the reason that the variable stiffness regions 50 protrude outward, it is also possible the wearer to pinch these protruding regions 50 when it is desired to pull up or down the diaper 1. In addition, for the reason that the variable stiffness regions 50 are provided with none of the elastics and the tightening force exerted on the wearer's body can be partially alleviated, the diaper 1 can be easily expanded outward in the transverse direction X. In this regard, it is essential for the front and rear waist regions as a whole to ensure a tightening force sufficient to keep the diaper 1 in close contact with the wearer's body. For this purpose, the tightening force of the regions other than the variable stiffness regions may be adjusted to ensure the requirements such as fit to the wearer's body.

The dimension of the respective variable stiffness regions 50 in the longitudinal direction Y may be in a range of about 20 to about 35 mm. If this dimension is less than 20 mm, the regions adapted to be folded will be lessened, resulting in that it will be impossible to ensure the sufficient ventilation and, at the same time, it will become correspondingly difficult to pinch these regions 50. If this dimension exceeds 35 mm, respective areas of the regions lying on each side inner and outer than the variable stiffness regions 50 as viewed in the longitudinal direction Y and adapted to be provided with the front and rear waist elastics 18a, 19a and the front and rear waist-opening elastics 28, 29 will be unacceptably restricted and eventually the sufficient tightening force of the diaper 1 to be exerted on the wearer's body may not be ensured.

Compared to the dimension in the longitudinal direction Y of the respective variable stiffness regions 50, namely, the distance between the front and rear waist elastics 18a, 19a and the front and rear waist-opening elastics 28, 29, which cooperate to lay out the respective variable stiffness regions 50, the distances (pitches) in the longitudinal direction Y at which the front and rear waist elastics 18a, 19a and the front and rear waist-opening elastics 28, 29 are respectively arranged are set to be relatively small. As a result, the front and rear waist regions 2, 3 can be more easily folded along lines extending in the transverse direction X in the variable stiffness regions 50 than the remaining regions.

The dimension in the longitudinal direction Y of the low stiffness sub-regions 51, 52 may be in a range of about 1 to about 10 mm. If this dimension is less than 1 mm, it will be difficult to fold the front and rear waist regions 2, 3 along these sub-regions and, if this dimension exceeds 10 mm, it will be difficult to ensure the required strength and the front waist region 2 and/or the rear waist region 3 likely be torn.

The variable stiffness region 50 in the front waist region 2 is formed in an area defined between the waist-opening 5, i.e., the boundary 23 of the front waist-opening sheet 21 and the line at the distance of about 32 mm from the boundary 23 toward the side of the crotch region 4 and the variable stiffness region 50 in the rear waist region 2 is formed in an area defined between the waist-opening 5, i.e., the boundary 23 of the rear waist-opening sheet 22 and the line at the distance of about 72 mm from the boundary 23 toward the side of the crotch region 4. In this way, the locations in which the respective variable stiffness regions 50 are formed may be differentiated from each other depending on whether the location is in the front waist region 2 or the rear waist region 3 and thereby the locations at which the voids are formed may be displaced from each other. Thus, the ventilation effect between inside and outside of the diaper 1 can be further efficiently achieved through the both waist regions and thereby humidity within the diaper 1 can be further decreased.

While the front and rear outer sheets 11, 12 are spaced apart from each other in the longitudinal direction Y in the illustrated embodiment, it is not essential for the outer sheet to include two separate sheets being spaced apart from each other, and it is possible to use a single continuous outer sheet for the front and rear waist regions. This invention has been described above on the basis of the embodiment in the form of a pull-on pants-type diaper having the front and rear waist regions 2, 3 previously bonded to each other along the respective lateral edges 7, this invention is applicable also to an open-type diaper having the front and rear waist regions not previously bonded to each other along the respective lateral edges.

The constituent members of the diaper 1 are not limited to those described in the specification but the other types of material widely used in the relevant technical field may be used without limitation. The terms "first" and "second" used in the description and claims of this invention are used merely to distinguish similar elements, similar positions or other similar means.

REFERENCE SIGNS LIST 1 diaper (disposable wearing article)
2 front waist region
3 rear waist region
4 crotch region
5 waist-opening
6 leg-openings
7 lateral edges
8 front end
9 rear end
10 chassis
11 front outer sheet (outer sheet)
12 rear outer sheet (outer sheet)
13 inner sheet
18a front waist elastics (waist elastics)
18b front leg elastics (waist elastics)
19a rear waist elastics (waist elastics)
19b rear leg elastics (waist elastics)
21 front waist-opening sheet (waist-opening sheet)
22 rear waist-opening sheet (waist-opening sheet)
23 boundaries
24, 25 first sheet segments
26, 27 second sheet segments
28 front waist-opening elastics (waist elastics)
29 rear waist-opening elastics (waist elastics)
30 absorbent structure
50 variable stiffness region
51, 52 low stiffness sub-regions
53, 54 inner high stiffness sub-regions (high stiffness sub-regions)
55, 56 outer high stiffness sub-regions (high stiffness sub-regions)
X transverse direction
Y longitudinal direction

The invention claimed is:
1. A disposable wearing article having a longitudinal direction and a transverse direction, the article comprising:
   a skin-contacting side;
   a garment-contacting side opposite to the skin-contacting side;
   a chassis including a front waist region, a rear waist region and a crotch region extending between the front and rear waist regions;
   an absorbent structure lying at least in the crotch region;
   a waist-opening defined by front and rear ends of the chassis; and
   leg-openings defined by lateral edges of the chassis, wherein a plurality of front and rear waist elastics extending in the transverse direction and spaced apart from each other in the longitudinal direction are contractibly attached under tension to the front and rear waist regions, wherein:
   the chassis includes a plurality of sheets layered upon one another;
   at least one of the front and rear waist regions is formed with a variable stiffness region including a low stiffness sub-region extending in the transverse direction and a pair of high stiffness sub-regions adjacent to both sides of the low stiffness sub-region in the longitudinal direction, wherein the variable stiffness region is bordered by a pair of the waist elastics in the corresponding waist region; and
   the chassis comprises an inner sheet lying on the skin-contacting side, an outer sheet lying on the garment-contacting side and a waist-opening sheet adapted to define the waist-opening in said at least one of the front and rear waist regions;
   the waist-opening sheet comprises a first sheet segment lying on the garment-contacting side, a second sheet segment lying on the skin-contacting side and a bound- ary lying between the first and second sheet segments so as to coincide with the waist-opening;

the first sheet segment overlaps both the inner sheet and the outer sheet, the second sheet segment overlaps the inner sheet, and the second sheet segment and the outer sheet are arranged so as to be spaced apart from each other in the longitudinal direction; and the low stiffness sub-region is defined by a region in which the second sheet segment and the outer sheet are spaced apart from each other, and the respective high stiffness regions are defined by a region in which the first sheet segment, the second sheet segment and the inner sheet are overlapped and by a region in which the first sheet segment, the outer sheet and the inner sheet are overlapped, such that the number of the sheets overlapped to form the low stiffness sub-region is fewer than the number of the sheets to form the respective high stiffness sub-regions.

2. The disposable wearing article according to claim 1, wherein a distance at which the pair of the waist elastics bordering the variable stiffness region is arranged is larger than those at which the other waist elastics lying outboard of the variable stiffness region in the longitudinal direction are arranged.

3. The disposable wearing article according to claim 1, wherein the waist elastics bordering the variable stiffness regions lie so as to overlap ends of the layered sheets.

4. The disposable wearing article according to claim 1, wherein a dimension in the longitudinal direction of the low stiffness sub-region is in a range of 1 mm to 10 mm.

5. The disposable wearing article according to claim 1, wherein a dimension in the longitudinal direction of the variable stiffness regions is in a range of 20 mm to 35 mm.

* * * * *